United States Patent [19]
Yeh

[11] Patent Number: 4,932,788
[45] Date of Patent: Jun. 12, 1990

[54] MONITORING OF THE QUALITY OF A FLOWING VAPOR

[76] Inventor: George C. Yeh, 2 Smedley Dr., Newtown Square, Pa. 19073

[21] Appl. No.: 308,011

[22] Filed: Feb. 9, 1989

Related U.S. Application Data

[63] Continuation-in-part of Ser. No. 839,034, Mar. 12, 1986, abandoned.

[51] Int. Cl.$^5$ .................. G01K 17/12; G01N 25/60
[52] U.S. Cl. ............................ 374/35; 73/861.04; 374/42
[58] Field of Search .................. 374/35, 31, 40, 42, 374/134, 29, 36; 73/202, 29, 861.04

[56] References Cited

U.S. PATENT DOCUMENTS

| | | |
|---|---|---|
| 3,479,872 | 11/1969 | Tauson . |
| 3,559,482 | 2/1971 | Baker et al. . |
| 4,210,278 | 7/1980 | Obler . |
| 4,561,785 | 12/1985 | Long et al. . |
| 4,618,266 | 10/1986 | Feller . |
| 4,668,102 | 5/1987 | Mott . |
| 4,672,561 | 6/1987 | Katayama et al. . |
| 4,681,466 | 7/1987 | Chien et al. . |

*Primary Examiner*—Daniel M. Yasich
*Attorney, Agent, or Firm*—Howson and Howson

[57] ABSTRACT

An improved monitoring of the quality and heat value of a flow of condensable vapor. A small side stream of representative vapor sample is tapped from the flow in the vapor main by utilizing the difference between the dynamic pressure of the vapor at a sample intake point and the suction pressure of the vapor at a sample return point. The sample stream passes through a superheater-calorimeter to completely vaporize any liquid entrained in the sample stream and superheat the vaporized sample, and then through a mass flowmeter before being returned to the vapor main. The quality and the heat value of the sample stream are determined by a heat balance around the superheater-calorimeter using correlations relating thermodynamic properties of the vapor to pressures and temperatures. The invention also monitors the enthalpy and the mass-flow rate of said vapor flow.

20 Claims, 4 Drawing Sheets

MONITORING OF THE QUALITY OF A FLOWING VAPOR

CROSS-REFERENCE TO RELATED APPLICATION

The present application is a continuation-in-part of U.S. patent application Ser. No. 06/839,034 filed Mar. 12, 1986 now abandoned.

BACKGROUND OF THE INVENTION

1. Field of the Invention

This invention relates generally to determining the quality and/or the heat value of a condensable vapor; and more particularly to methods and apparatus for continuously monitoring the quality and/or the heat value of a flowing vapor such as steam by representative sampling, calorimetric measurement, and mass flow measurement.

2. Description of Prior Art

The quality of condensable vapor, such as steam, is ordinally determined by a calorimeter. The most common types of the steam calorimeter, arranged according to their known accuracy, are: throttling, separating, combined throttling and separating, electric, and barrel calorimeters. Except the separating calorimeter, the common process of these calorimetric methods is that the measurements are made at a lower energy level than that of the original sampling conditions and that it is assumed that the kinetic energy of the high-velocity steam is all returned as heat in the fluid when it is brought to rest in the low-pressure downstream calorimeter chamber for the determination of quality. In case of the throttling calorimeter, the readings can be used if there is superheat at this point. If there is no superheat present in the calorimeter chamber at atmospheric pressure, the chamber must be connected to a vacuum source to extend the range of expansion; or a device, such as a separating calorimeter, must be used in which the liquid is mechanically separated from the vapor and measured. Since it it not always clear whether or not superheat is present in the calorimeter chamber of a throttling calorimeter, and the accuracy of the separating calorimeter is unsatisfactory, the limits of moisture within which the throttling calorimeter will work at sea level are known to be from 2.88% at 50 psi to 7.3% at 400 psi. Furthermore, at least 10° F. superheat must be obtained by the expansion for results within ±50% accuracy. Therefore, the throttling calorimeter is considered inadequate for determining steam quality at pressures above 400 psi.

The above common types of steam calorimeter require bleeding off a side stream of vapor sample, which is led to the atmosphere after passing through the calorimeter chamber. As a result, the measurements taken may be erroneous if a thermal equilibrium state has not been reached within the calorimeter before taking readings. The hot vapor sample bled off can cause a nuisance to the operator nearby and represents a loss of the vapor also. The barrel calorimeter involves a considerable expenditure of time and labor and it is not suitable for rapid determination of the vapor quality of transient flow systems. The conventional electric calorimeter for the intermittent determination of steam quality or the continuous flow type electric calorimeter has a serious drawback in common—both assume that the latent heat of vaporization and/or the specific heat of vapor is independent of temperature and pressure in determination of vapor quality. This inventor has found that both latent heat of vaporization and specific heats of all vapors are strongly dependent on temperature changes although they are less sensitive to pressure changes, as will be seen from the correlations developed by the inventor and disclosed hereinafter.

It is important to point out that in order to obtain accurate results calorimeters should be made to obtain a truly representative sample of the flowing vapor. The design of sampling device used and its location are important factors in obtaining a representative sample. The Power Test Code of the American Society of Mechanical Engineers recommends a sampling nozzle made of ¼ or ⅜-inch pipe, closed at the inner end and having the portion of the nozzle inside the steam main drilled with ⅛-inch holes spaced on ½ inch centers for steam mains up to 6 inches in diameter. This sampling nozzle should be located in the main in such a position that the holes will directly face the steam flow. The above design of sampling nozzle has become a standard practice in the industry although it is doubtful whether a representative sample is always obtained using a sample nozzle of the above design, as the composition of the total sample taken is affected by several factors including the radial distribution of entrained liquid, the vapor pressure and velocity, the pressure drop of vapor sample entering each sampling hole, etc. All these factors have not been fully taken into consideration previously in the design and location of sampling nozzle.

In addition to the calorimetric methods described above, many two phase flow measurement techniques, which may be related to the determination of vapor quality, have been investigated and evaluated by the present inventor. These include the measurement techniques of pressure, pressure differential, fluid temperature, density and void fraction, flow regime and void distribution, velocity slip, etc. The results of the above investigation and evaluation indicate that while some categories of these techniques require the development of implementation designs and operating techniques in order to avoid the adverse effects of the normally hostile environment of the transient two-phase, high-pressure, high-temperature conditions associated with power plant safety tests, other categories need considerable developments and improvements in the actual design and the fundamental understanding of the operating characteristics. None of the above two-phase flow measurement techniques was found to be capable of accurately monitoring the quality and enthalpy of a condensable vapor flow.

SUMMARY OF THE INVENTION

In view of the above, the main objects of the present invention are to provide a system capable of monitoring accurately the quality and the enthalpy of a flowing vapor, such as steam and alkali metals (for example, sodium, potassium, and cesium) and at the same time meeting with the following requirements and conditions: (1) said system must respond to rapid changes in the quality and enthalpy of the flowing vapor; (2) said system must be capable of accurate measurement over wider ranges of parameter spans than is required for present industrial or laboratory application; (3) said system must be designed, constructed and operated to produce a continuous, small side stream of representative sample for taking the necessary measurements and then returning the sample to the vapor main without bleeding off the same to the atmosphere; (4) said system must be able to use sensors which can respond rapidly and accurately to any changes in temperature and pressure of the vapor sample and are interpretable regardless of the characteristics of the flowing vapor at the point of sampling and measurements in the vapor main; (5) said system must cause no or negligible disturbance to the flow regime inside the vapor main; (6) said system must not affect the thermodynamic properties of the flowing vapor to any degree by changing its temperature and/or pressure, or causing a phase change; (7) said system must be able to service under severe over-range conditions and still function at the prescribed conditions; (8) said system must not degrade from their calibrated state for the duration of test interval; (9) said system must be capable of reliable performance over long periods without adjustment or service, for long-term testing; (10) said system must be able to perform where accessibility for service or signal conditioning is limited; (11) said system must be able to be calibrated before installation into the actual test assembly, if necessary; (12) said system must be able to operate in hostile environments; such as high temperature and pressure, radiation, corrosion, vibration, and severe transient mechanical loads; (13) said system must not cause any personal hazards; and (14) finally, said system must be so designed that it is readily programmable and controlled by a computer.

Briefly, these objects are accomplished with a small side stream of representative sample tapped off the vapor main by utilizing the difference between the dynamic pressure of the vapor at the sample intake point and the suction pressure of same at the sample returning point. The sample stream is first passed through a superheater-calorimeter to vaporize completely any liquid entrained in the sample stream and to superheat the vaporized sample, and then the sample stream is passed through a mass flowmeter before being returned to the vapor main. To assure a continuous flow of truly representative sample of the vapor main, the sampling device is designed, constructed, and positioned according to the principles of "equal annular mass flow" based on Bernoulli's law. To provide the maximum pressure difference between the sample intake point and the sample returning point, the sampling intake-nozzle is designed and positioned inside the vapor main in such a way that the inlet holes will face the opposite direction of the vapor flow (upstream) and the outlet holes of the sample returning-nozzle will face the same direction of vapor flow (downstream). In this way, the vapor sample will flow into the inlet holes of the sample intake-nozzle under the dynamic pressure of vapor main and will flow out the outlet of holes of the sample returning-nozzle under the suction pressure of vapor main; thus no pump is needed to maintain the continuous flow of vapor sample through the entire monitoring system, under normal conditions of operation.

The method for calculating the quality and/or the heat value of vapor is by the use of a heat balance around the superheater-calorimeter. The above heat balance and correlations relating the latent heat of vaporization to the saturation pressure and the saturation temperature of steam were developed. A correlation relating the saturation temperature to the saturation pressure of steam was also developed. Using the correlation developed by the inventor for predicting the specific heat and enthalpy of steam at different pressures and temperatures, it was found that the specific heat can be calculated accurately at pressures between 100 psia and 3100 psia for steam which goes through pressure and temperature changes in the stated pressure range. This was essential to the solving of the heat balance because the steam when superheated in the superheater-calorimeter, goes through both pressure and temperature changes. For obtaining the enthalpy of the sample prior to the superheating in the calorimeter, correlations were developed relating the enthalpy of saturated vapor and of water to saturation pressure and also to saturation temperature. Finally, a computer program (mathematical model) was written and run incorporating the above necessary correlations and input variables to simulate "on-line" operation for assessing the quality and the heat value of steam.

Through computer simulation and experimentation it was observed that the accurate measurement of steam quality and enthalpy of the sample can be made. It should be noted that the results of the above computer simulation indicated that accurate temperature and mass-flow rate readings are critical in obtaining and monitoring the steam quality and enthalpy accurately. The correlation and therefore the mathematical model are less sensitive to pressure measurement. When accurate readings of temperature and mass-flow rate are taken, the steam quality can be found to within $\pm 2.0\%$; the enthalpy of the sample can be found to within 1.0% of the literature values. The computer program model can be transferred to accept temperature and pressure readings from transducers without changing its performance.

BRIEF DESCRIPTION OF THE DRAWINGS

For a better understanding of these and other objects and aspects, reference may be made to the following detailed description taken in conjunction with the accompanying drawings wherein.

DETAILED DESCRIPTION OF THE INVENTION

Figure 1:
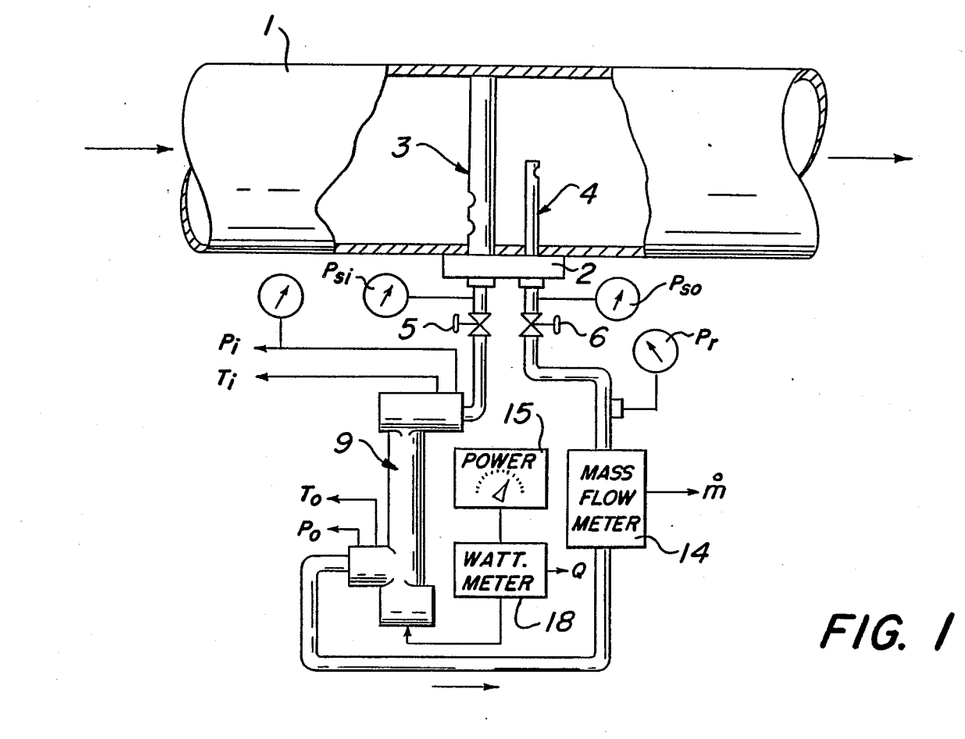
FIG. 1 is a schematic diagram of a system according to the invention for determining the quality and the enthalpy of a flowing vapor.
Figure 3:
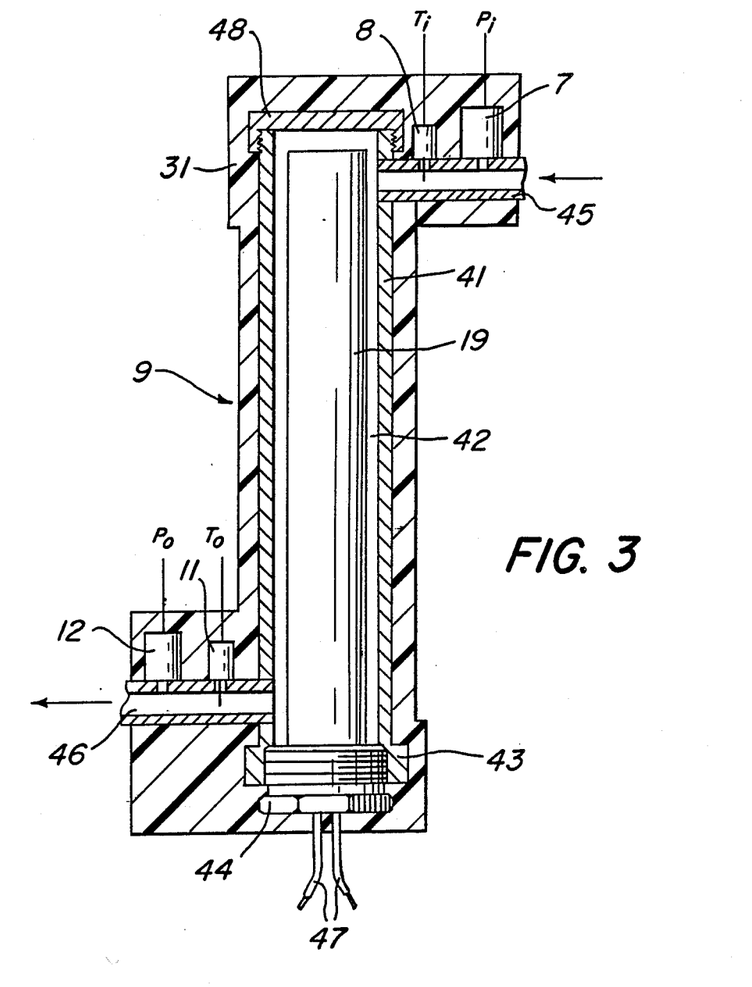
FIG. 3 is a view in cross-section of a superheater-calorimeter in the system of FIG. 1.

Referring now to the drawings wherein like characters designate like or corresponding parts throughout the several views, there is shown in FIG. 1, vapor flowing in the direction shown by arrows in a vapor main 1. The sampling device comprises a sample intake nozzle 3 and a sample return nozzle 4 secured in place by a mounting head 2 externally fixed to the vapor main 1, and 20 facilitate the insertion and removal from vapor main 1, when necessary. The vapor sample flowing into intake nozzle 3 is passed through a manually adjustable flow regulating valve 5 to a superheater calorimeter 9, where the vapor sample is heated internally with an electrical heater 19 to become completely superheated, then through a conventional mass flowmeter 14, and finally through a manually adjustable valve 6 for returning to vapor main 1 at return nozzle 4. As shown in FIG. 3, the inlet pressure $P_i$ and temperature $T_i$ of the sample to calorimeter 9 are measured by pressure and temperature transducers 7 and 8, respectively; and the outlet temperature $T_o$ and pressure $P_o$ by transducers 11 and 12, respectively. Heater 19 is energized through electrical conductor 13 by an adjustable power supply 15 and the amount of power input in terms of heat is measured at wattmeter 18. The amount of heat Q added must be sufficient to raise the outlet temperature $T_o$ to a value greater than inlet temperature, $T_i$, thereby ensuring that all moisture in the sample stream has been completely vaporized to a superheated condition. Temperature transducers 8 and 11 are preferably thermistors of the thin-band type placed around the pipe carrying the sample stream and in order not to obstruct the stream. Mass flowmeter 14 is preferably an electrothermal flowmeter of the boundary-layer type, such as Model 60 Thermal Flowmeter disclosed in Technical Bulletin 682-D of Thermal Instrument Company, Trevose, Penn. 19047, in which the mass flow rate m of the sample is measured and transmitted by elements outside the pipe carrying the sample stream in order not to obstruct the stream. Of course, other types of mass flowmeters may be employed. The principle of operation of the electrothermal mass flowmeter is well known. See Cheremisinoff, N. P., "Applied Fluid Flow Measurement" Marcel Dekker, Inc., N.Y. (1977), pp. 143–146. A determinable amount of heat is injected into the flowing sample through the walls of the flowmeter pipe and the boundary layer. The initial temperature of the sample and the downstream temperature across the boundary layer are sufficient for satisfactory operation. Two methods normally employed to measure the mass flow rate $\dot{m}$ are the variable temperature and the variable power techniques. In general, the response time is considered fast and may vary from a fraction of a second to a few seconds, depending on the velocity of vapor and the thickness of the section wall. Measurements of flow rates over large ranges (total ranges 1200 to 1) can be made with this type of mass flowmeter by using a single transducer with proper heating and transmitting circuits. The measurement error is small for small changes in specific heat and thermal conductivity of superheated sample vapor, and automatic compensation can be added for significant changes in the above properties of vapor, utilizing the vapor temperature $T_o$ and the vapor pressure $P_o$ monitored by transducers 11 and 12 separately as the vapor enters flowmeter 14. The correlations developed by the inventor, which will be discussed hereinafter, can be used to predict the specific heat Cp of vapor. As the vapor sample leaving said mass flowmeter 14 the pressure $P_R$ is measured at transducer 10. The driving force needed for the vapor sample stream to flow through the entire monitoring system is provided by the difference between the dynamic pressure of the vapor at intake nozzle 3 and the suction pressure of same at the return nozzle 4.

Figure 4A:
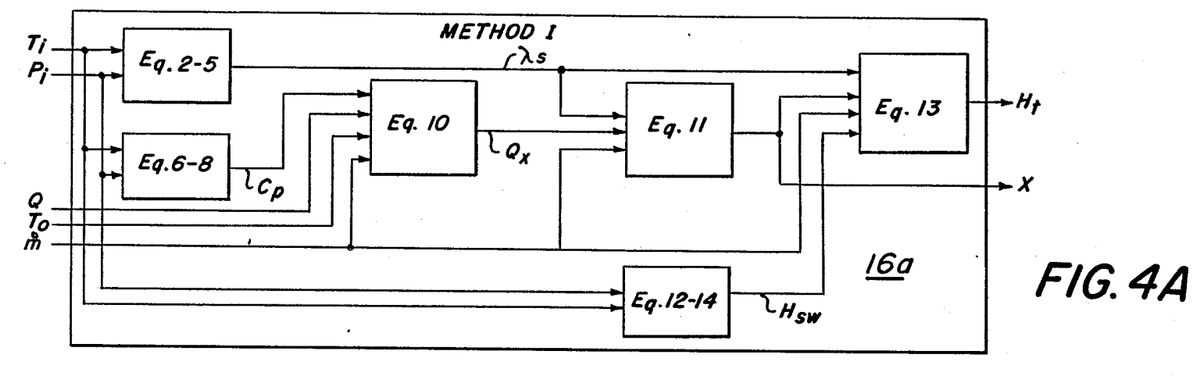
FIGS. 4A and 4B are functional block diagrams of two computer embodiments utilized in the system of FIG. 1.
Figure 4B:
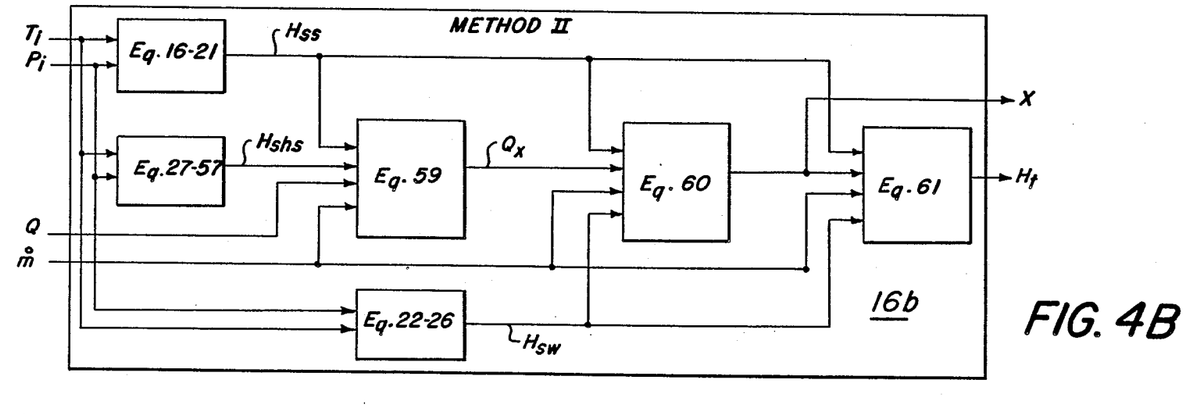

The output signals $T_i$ and $T_o$ from temperature transducer 8, signal $P_i$ from pressure transducer 7 signal $\dot{m}$ from mass flowmeter 14, and signal Q from watt meter 18 are all fed into a computer 16a or 16b, FIG. 4A or 4B, for determining the quality X and enthalpy $H_t$ of the sample vapor. Computer 16a or 16b is a conventional general purpose system, such as the VAX Model VAX-ENG 6210 or a modern microcomputer with sufficient memory, programmed according to well-known techniques to execute the necessary methematical computations as described hereinafter. Obviously other properties of the vapor, can be recorded and displayed as may be desirable. Computer 16 permits an operator to program the system for desired operating ranges of temperature, pressure, and mass flow rate of the sample stream, and store and recall any information relating to the stream, which represents the vapor main. The flow rate of vapor main can also be related to the flow rate of sample stream, as may be obvious.

Figure 2:
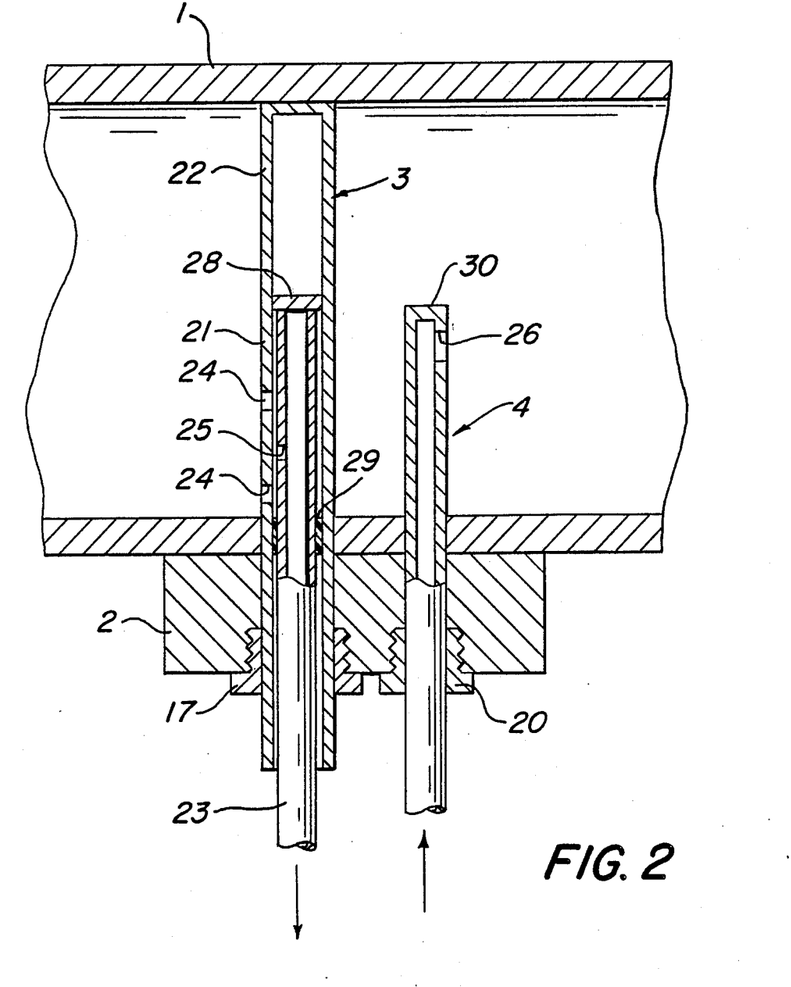
FIG. 2 is a view in cross-section of a sampling device in the system of FIG. 1.

Referring to FIG. 2, intake nozzle 3 includes an outer tube 21, with two holes 24 so located that when said nozzle 3 is inserted into the vapor main 1 in the right position their centers represent equal annular mass flow rates of the vapor main, from which a representative sample is to be taken. The location of holes 24 must be determined by first determining the mass flow rates or pressures of various annular segments of the vapor main and then distributing holes 24 in such way that their centers will represent equal annular mass flow rates. In most applications, the assumption of turbulent flow conditions may be valid. Nozzle 3 also includes a concentric inner tube 23 with at least one hole 25 located at the midpoint between holes 24 so that the vapor sample taken into each hole 24 will travel the same distance to reach hole 25 of the inner tube, where all the vapor samples are combined into a single stream before flowing through various measurement points in the monitoring system. A plug 28 placed on the inner end of tube 23 is position to coincide with the center of the vapor main, and seal ring 29 placed in the annular space between tubes 21 and 23 direct the incoming vapor sample to hole 25. In order to produce geometric, dynamic, and kinematic similarities in the vicinity of sample intake nozzle 3, external tube 21 has an extension 22 reaching to the side of wall of the vapor main diametrically opposite of its insertion, so that the flow pattern of vapor in front of the tube 21 will be similar across the entire diameter of the vapor main. While holes 24 in tube 21 faces upstream a hole (or holes) 26 in the return nozzle 4 faces downstream. The nozzle 4 is closed at the inner end 30 so that the vapor returning to the vapor main will leave from the hole 26, at which a suction pressure is produced by the kinetic energy of the flowing vapor. Screw plugs 17 and 20 provide a seal between the mounting head 2 and nozzles 3 and 4 to facilitate their insertion and removal from the vapor main 1 when necessary.

The velocity, pressure, and kinetic energy of the sample stream flowing through the entire monitoring system can be analyzed by the use of the well-known Bernoulli Equation, which is based on the first law of thermodynamics. Thus, it may be readily be shown that the sample stream truly represents the flowing vapor being monitored.

Obviously, both the sample intake and return nozzles 3 and 4 may be placed together inside a large pipe with a single screw plug for easier installation and greater mechanical strength to withstand the highly turbulent conditions of stream main.

Referring to FIG. 3, superheater-calorimeter 9 includes an elongate shell 41 with heater 19 communicating between inlet pipe 45 and outlet pipe 46. Heater 19 is secured at its electrical terminals 47 by a screw plug 44 in a mounting head 43 at one end of shell 41 to form an annular space 42. A screw cap 48 at the other end of shell 41 is provided to facilitate the periodic cleaning of the calorimeter interior. Pressure transducer 7 and the temperature transducer 8 are mounted on inlet pipe 45 and, similarly, temperature transducer 11 and pressure transducer 12 are mounted on outlet pipe 46 for exposure to the vapor sample. Calorimeter 9 is completely covered by a thermal insulator 31 to prevent any heat flow between calorimeter 9 and the surroundings to ensure accurate measurements. The heat input Q to calorimeter 9 is accurately controlled and measured by power supply 15 and wattmeter 18 for maintaining a predetermined temperature rise in steam flowing through calorimeter 9.

The principles and operation of the invention will be now discussed further by examples for determining the quality X and the enthalpy $H_t$ of a flowing steam.

EXAMPLES

As shown in the following, the heat balance around the superheater-calorimeter 9 may be accurately determined in computer 16 by one or two different methods: (1) by the use of latent heat of vaporization of saturated liquid $\lambda_s$ and the specific heat of superheated vapor $C_p$, and (2) by the use of the enthalpies of saturated liquid $H_{sw}$, of saturated vapor $H_{ss}$, and of superheated vapor $H_{shs}$. Therefore, examples of the present invention will be shown for each of these two methods used, for flowing steam.

I. BY THE USE OF LATENT HEAT OF VAPORIZATION OF SATURATED LIQUID AND SPECIFIC HEAT OF SUPERHEATED VAPOR (1) Methods of Calculation A heat balance around the superheater-calorimeter 9 provides the information that can be utilized by computer 16a to determine the quality X of the sample stream. Data that are needed are the inlet and outlet temperatures $T_i$ and $T_o$ of superheater-calorimeter 9, incoming pressure $P_i$, the mass flow rate m of the sample stream, and the heat Q added to the sample by the calorimeter 9. The heat Q added to the sample is used first to vaporize any moisture present in the sample, and then to superheat the vapor. The heat balance around the superheater-calorimeter can be expressed by:

$$Q = \dot{m}(1 - x)\lambda_s + \dot{m} \int_{T_i}^{T_o} C_p dT \quad (1)$$

where
Q=heat input by the calorimeter (BTU/hr),
$\dot{m}$=mass flow rate of the sample (lb/hr),
$\lambda_s$=latent heat of vaporization (BTU/lb),
X=mass fraction of the sample that is vapor,
$C_p$=specific heat of the steam (BTU/lb, °F.),
$T_i$=inlet temperature of the calorimeter (°R), and
$T_o$=outlet temperature of the calorimeter (°R).

The inlet and outlet temperatures $T_i$ and $T_o$, mass flow rate m, inlet and outlet pressures $P_i$ and $P_o$, and heat Q added to the sample will be monitored continuously. The latent heat of vaporization $\lambda_s$ (BTU/lb) is calculated from the saturation pressure $P_s$ (psia) at the inlet temperature $T_i$ in the following manner:

$$\lambda_s = 10^{-0.00014661(Ps)+2.9525495} \quad (2)$$

The latent heat $\lambda_s$ (BTU/lb) can also be calculated from the saturation temperature $T_s$ (°R) at the inlet pressure $P_i$ from these correlations:

$$\lambda_s = 10^{-0.0004381(Ts)+3.2929282}, \text{ or} \quad (3)$$

$$\lambda_s = 10^{-0.0006944(Ts)+3.5209725} \quad (4)$$

Equation 3 is used for saturation temperatures $T_s$ between 741° R (281° F.) and 900° R (440° F.), and Equation 4 is used for saturation temperatures $T_s$ above 900° R (b 440° F.). The saturation pressure $P_s$ correlation of Equation 2 is used preferably because it covers all pressures greater than 100 psia and only one equation need be used. The saturation temperature $T_s$ (°R) is found to be a function of the saturation pressure $P_s$ (psia) for a range between 100 psia and 1000 psia.

$$T_s = 118.77781 (P_s)^{0.22036511} + 460 \quad (5)$$

The definite integral, $\int C_p dT$, can be evaluated with $C_p$ as a function of temperature.

$$C_p = C_1 + C_2 (1/T) \quad (6)$$

Constants $C_1$ and $C_2$ in the above equation for various pressures ranging from 200 psia to 1000 psia are a function of inlet pressure $P_i$ (psia):

$$C_1 = -0.00039529 (P_1) + 0.5171495, \text{ and} \quad (7)$$

$$C_2 = 4.5032194 (P_1) - 109.69898 \quad (8)$$

Equation 6 can be integrated with respect to temperature:

$$\int_{T_i}^{T_o} \left( C_1 + C_2 \frac{1}{T} \right) = (C_1 T + C_2 \ln T) \bigg|_{T_i}^{T_o} \quad (9)$$

The definite integral when multiplied by the mass flow rate m is the amount of heat used for superheating the sample after the sample had been completely vaporized. The difference between the amount of heat Q put into the sample by the superheater-calorimeter 9 and the amount of heat used in superheating the sample $$\dot{m} \int_{T_i}^{T_o} C_p dT$$

is the amount of heat $Q_x$ (BTU/lb) that was used to vaporize the moisture present in the sample:

$$Q_x = Q - \dot{m} \int_{T_i}^{T_o} C_p dT \quad (10)$$

The mass fraction X of the sample that was vapor when entering the superheater-calorimeter 9 is found by $$X = 1 - \frac{Q_x}{\dot{m}\lambda_s} \quad (11)$$

This amount, X, when converted to a percentage is the quality of steam.

The enthalpy of the steam entering the superheater-calorimeter 9 can also be calculated. A correlation has been developed for obtaining the enthalpy of saturated water $H_{s.w.}$ (BTU/lb) from the saturation pressure $P_s$ (psia) at inlet temperature $T_i$:

$$H_{s.w.} = 90.7607 (P_s)^{0.2573} \quad (12)$$

When the quality X has been calculated and the amount of moisture in the sample known, the total enthalpy of the sample $H_t$ (BTU/lb) can be calculated as follows:

$$H_t = \dot{m}H_{s.w.} + \dot{m}X\lambda_s \qquad (13)$$

The enthalpy of saturated liquid $H_{s.w.}$ (BTU/lb) can also be obtained from the saturation temperature $T_s$ (°R) at inlet pressure $P_i$ (psia) from the following correlation:

$$H_{s.w.} = 0.0000165 \, (T_s)^{2.5064} \qquad (14)$$

(2) Computer Simulation

Referring to FIG. 4A a computer program has been developed to calculate the steam quality X and enthalpy $H_t$ with a system interactive with a general purpose computer 16a and can be adapted to accept readings from the required sensors. The equations identified in the blocks within computer 16a of FIG. 4A correspond to the functions defined by the Equations 2 through 14, supra. The program was written first in Fortran language.

Data needed for simulation of on-line operation are the inlet temperature and pressure $T_i$ and $P_i$, the outlet temperature $T_o$ of superheater-calorimeter 9, the mass flow-rate $\dot{m}$, and the heat Q added to the sample by calorimeter 9. These values enable determination of the saturation temperature $T_s$ from steam tables stored in memory, the latent heat of vaporization $\lambda_s$, the heat $Q_x$ used for superheating the sample, the enthalpy $H_t$ and the quality X of the steam.

Under circumstances of steam that is of less than 100% quality, the incoming temperature $T_i$ will be most likely the saturation temperature $T_s$. However, it is desirable to monitor the incoming temperature for two reasons. First, the saturation temperature $T_s$ is derived from the saturation pressure $P_s$ and is not exact ($\pm 1\%$); and secondly, in the event that the steam sample is already superheated, the incoming temperature $T_i$ would be greater than the saturation temperature $T_s$.

Accurate temperature readings are most important as the integral $\int C_p dT$ is most sensitive to temperatures, and it is essential that in evaluating the integral that the temperatures used be the actual inlet and outlet temperatures $T_i$ and $T_o$. Computer runs show that when temperatures monitored are $\pm 5\%$ of actual, the quality X calculated is affected by $\pm 2\%$. It is not as sensitive to pressure readings because the specific heat of superheated steam is not as strong a function of pressure as it is of temperature. When $\pm 5\%$ errors are introduced in the pressure readings, the quality is calculated remains relatively unchanged by the errors.

The quality X determination is accurate, as shown below in Tables 1, 2, and 3. Qualities exceeding 100% are due only to the fact that the term $\int C_p dT$ calculated is slightly larger than the actual amount of heat input by the superheater-calorimeter. This is due to the calculation of specific heat of steam $C_p$ not being exact but $\pm 1\%$ by the correlation used.

The computer program also calculates by Equation 13 the total enthalpy $H_t$ of the sample before entering the superheater-calorimeter 9. Using correlation of Equation 12, the enthalpy of the saturated liquid $H_{sw}$ is calculated. Added to this is the latent heat of vaporization $\lambda_s$ contained in the vapor entering. As shown in Tables 1, 2, and 3, the amount of vapor entering is accurate within $\pm 2\%$ except when the mass flow rate m is erroneous by $\pm 5\%$. This calculation is most sensitive to the mass flow rate m because both the enthalpy of saturated liquid $H_{sw}$ and the latent heat of vaporization $\lambda_s$ are multiplied by this measurement in finding the enthalpy $H_t$ of the sample.

(3) Results and Analysis

For analysis of the performance of the present invention including the computer program written incorporating the above correlations, a series of simulation runs in three different sets were made.

The first set of simulations, a series of five runs, was most general. The objective of this set of tests was to see how well the program and correlations performed over a broad range of conditions. Data were taken from the steam tables for the following sets of conditions: first, a large pressure change $P_i - P_o$ and a large temperature change $T_i - T_o$ through the superheater-calorimeter 9 were assumed; secondly a small pressure change $P_i - P_o$ and a large degree of superheating in and out of the superheater-calorimeter 9 were assumed. The third run considered a poor entering steam quality X. The fourth run considered an entering steam in a superheated state, and the fifth assumed that the steam entering the superheater-calorimeter 9 was at its saturation conditions. The results of the first set of tests are presented in Table 1. It was found that the methods of calculation and the computer would provide accurate results for the steam quality and enthalpy calculations using the correlations that were developed for this invention.

TABLE 1

| Through Superheater-Calorimeter | CONDITIONS | | | | ENTHALPY | | | QUALITY | | |
|---|---|---|---|---|---|---|---|---|---|---|
| | $P_i$ (psia) | $P_o$ (psia) | $T_i$ (°F.) | $T_o$ (°F.) | Hin (BTU/hr @ 10 lbs/hr) | Hin* | Δ % | X | X* (Calorimeter) | Δ % |
| 1 Large Pressure Large Temperature | 60 | 120 | 293 | 440 | 11,501 | 11,203 | −2.6 | 97.0 | 97.9 | 0.9 |
| 2 Small Pressure Large Superheat | 200 | 220 | 381 | 447 | 11,562 | 11,547 | −0.1 | 95.0 | 95.2 | 0.2 |
| 3 Poor Quality into | 500 | 550 | 467 | 495 | 9,630 | 9,728 | 1.0 | 68.0 | 69.2 | 1.8 |
| 4 Superheater into | 300 | 500 | 437 | 497 | 12,029 | | | 100.0 | 102.0 | 2.0 |
| 5 Saturated into | 400 | 450 | 445 | 495 | 12,046 | 12,165 | 1.0 | 100.0 | 101.0 | 1.0 |

*Values from computer simulations
Δ %: Error percent in simulation results

The second set of simulation runs used steam conditions that would be commonly encountered in industry. For each test run, a different combination of errors in pressure and temperature readings at both the inlet and the outlet of the superheater-calorimeter were assumed. Errors of $\pm 5\%$ were input to the computer in a series of six simulation runs. The objective of this set of runs was to see the effect of errors in measuring each variable on the accuracy of the simulated runs. The results of this test set are presented in Table 2. It was found that temperature readings had the largest effect because of the integration term in the heat balance equation around the superheater-calorimeter 9. Accurate temperature readings are crucial to the accuracy of calculations carried out in the simulation program. Errors of ±5% in the pressure readings had little effect on the accuracy of the steam quality measurement.

TABLE 2

| Steam Conditions: | |
|---|---|
| $P_i$ (psia) = | 200 |
| $P_o$ (psia) = | 220 |
| $T_i$ (°F.) = | 381 |
| $T_o$ (°F.) = | 447 |
| $\dot{m}$ (lbs/hr) = | 10 |
| Quality (%) = | 95 |
| Enthalpy (BTU/lb) = | 1156.2 |

| | | ENTHALPY | | QUALITY | |
|---|---|---|---|---|---|
| RUN | ASSUMED ERRORS | Hin (BTU/hr) | Δ % | X (percent) | Δ % |
| 1. | $\Delta P_i = +5\%$ | 11,573 | 0.1 | 95.56 | 0.6 |
| 2. | $\Delta P_i = -5\%$ | 11,530 | −0.5 | 95.49 | 0.5 |
| 3. | $\Delta P_o = +5\%$ | 11,556 | −0.05 | 95.58 | 0.6 |
| 4. | $\Delta P_o = -5\%$ | 11,548 | −0.1 | 95.47 | 0.5 |
| 5. | $\Delta T_o = +5\%$ | 11,686 | 1.1 | 97.12 | 2.2 |
| 6. | $\Delta T_o = -5\%$ | 11,414 | −1.2 | 93.87 | −1.2 |

Δ %: Error percent in simulation results

The third set of simulation runs was similar to the second except that the measuring errors were assumed to be ±1% of true values. The objective of this test was to see the performance of the invention under conditions in which it may be actually operating. Errors of 1% are a more realistic estimate of a real situation than 5% errors. Steam conditions of less than 100% quality and of superheated steam were used in this battery of tests. Also in this set, errors in the mass flow rate reading were introduced at two levels, ±1% and ±3%. The results of this test are presented in Table 3. As before, it was found that errors in temperature readings affect most the accuracy of the steam quality determination. However, even with temperature reading errors of ±1%, steam quality can be found within an accuracy of ±3%. Mass flow readings when off by ±5% cause a small effect on the steam quality determination, but greatly affect the calculation of the enthalpy of steam. This is due to the fact that the specific heat is multiplied by the mass flow rate in determining the enthalpy, and therefore any error introduced to the mass flow rate is multiplied in this method.

The calculation of steam qualities of greater than 100% has no actual significance. This is the result of the calculation of the integral $\int C_p \, dT$, when multiplied by the mass flow rate m, being slightly larger than the amount of heat Q added to the sample in the superheater-calorimeter 9. When this is the case, the difference found between the amount of heat added and amount used in superheating the sample is negative. A negative number is then subtracted (and therefore added) from 100 in the computer program, resulting in a calculated quality of greater than 100%.

TABLE 3

| Steam Conditions: | Below Saturation | Superheated |
|---|---|---|
| $P_i$ (psia) = | 380 | 400 |
| $P_o$ = | 450 | 500 |
| $T_i$ (°F.) = | 440 | 465 |
| $T_o$ (°F.) = | 496 | 547 |
| $\dot{m}$ (lbs/hr) = | 100 | 100 |
| Quality (%) = | 86 | 100 |

| | ERRORS | QUALITY (%) | | QUALITY (%) | |
|---|---|---|---|---|---|
| RUN | ASSUMED | X | Δ % | X | Δ % |
| 1. | $\Delta T_i = \Delta T_o = +1\%$ | 87.77 | 2.0 | 101.84 | 1.8 |
| 2. | $\Delta T_i = \Delta T_o = -1\%$ | 87.79 | 2.0 | 101.90 | 1.9 |
| 3. | $\Delta P_i = \Delta P_o = +1\%$ | 87.79 | 2.0 | 101.91 | 1.9 |
| 4. | $\Delta P_i = \Delta P_o = -1\%$ | 87.77 | 2.0 | 101.84 | 1.8 |
| 5. | $\Delta P_i = \Delta P_o = +1\%$ $\Delta T_i = \Delta T_o = +1\%$ $\Delta \dot{m} = +1\%$ | 87.78 | 2.0 | 101.93 | 1.9 |
| 6. | $\Delta P_i = \Delta P_o = -1\%$ $\Delta T_i = \Delta T_o = -1\%$ $\Delta \dot{m} = -1\%$ | 87.60 | 1.9 | 101.80 | 1.8 |
| 7. | $\Delta P_i = \Delta T_i = -1\%$ $\Delta P_o = \Delta T_o = +1\%$ $\Delta \dot{m} = +1\%$ | 88.89 | 3.4 | 102.86 | 2.9 |
| 8. | $\Delta P_i = \Delta T_i = -1\%$ $\Delta P_o = \Delta T_o = +1\%$ $\Delta \dot{m} = -1\%$ | 88.53 | 2.9 | 102.74 | 2.7 |
| 9. | $\Delta P_i = \Delta T_i = -1\%$ $\Delta P_o = \Delta T_o = +1\%$ $\Delta \dot{m} = +5\%$ | 89.56 | 4.1 | 103.10 | 3.1 |
| 10. | $\Delta P_i = \Delta T_i = -1\%$ $\Delta P_o = \Delta T_o = +1\%$ $\Delta \dot{m} = -5\%$ | 87.78 | 2.0 | 102.50 | 2.5 |
| 11. | None | 87.78 | 2.0 | 101.87 | 1.9 |

Δ %: Error percent in simulation results

In the present invention, steam will always be leaving the superheater-calorimeter 9 in a superheated state. This will be the case any time there is a temperature change through the superheater-calorimeter 9. If there were no temperature change, it would be impossible to tell if the steam sample had been fully vaporized or not. An increase in temperature assures a total vapor phase exiting the superheater-calorimeter 9. When the present invention is being used on line, a temperature change is what is to be sought when adjusting the heat input to the superheater-calorimeter 9. The heat input Q to the superheater-calorimeter 9 from power supply 15 can be measured and controlled with an accuracy of ±1.0% or better. Needless to say, this accuracy will reflect directly on the accuracy of the determination of the quality X and the enthalpy $H_t$ of a flowing vapor.

II. BY THE USE OF ENTHALPIES OF SATURATED WATER, OF SATURATED STEAM, AND OF SUPERHEATED STEAM (1) Methods of Calculation The latent heat of vaporization $\lambda_s$ (BTU/lb) is the difference between the enthalpy of saturated steam $H_{s.s.}$ (BTU/lb) and of saturated water $H_{s.w.}$ (BTU/lb) at the prevailing saturated temperature $T_s$ and pressure $P_s$, and may be written as follows:

$$\lambda_s = H_{s.s.} - H_{s.w.} \tag{15}$$

The enthalpy of saturated steam $H_{s.s.}$ may be calculated from the saturation pressure $P_s$ (psia) at inlet temperature $T_i$, by the following equations:

For saturation pressures, $P_s$, from 100 to 250 psia;

$$H_{s.s.} = 0.09137137 \, (P_s) + 1179.6703 \tag{16}$$

For saturation pressures, $P_s$, from 250 to 850 psia;

$$H_{s.s.} = 1202.5 \tag{17}$$

For saturation pressures, $P_s$, from 800 to 1500 psia;

$$H_{s.s.} = -0.042829374 \, (P_s) + 1235.5054 \tag{18}$$

For saturation pressures, $P_s$, from 1500 to 2200 psia;

$$H_{s.s.} = -0.068204761 \, (P_s) + 1273.9388 \tag{19}$$

For saturation pressures, 2200 to 2800 psia;

$$H_{s.s.} = -0.10996734 \, (P_s) + 1366.3420 \tag{20}$$

For saturation pressures, $P_s$, from 2800 to 3100 psia;

$$H_{s.s.} = 116003.54 \, (P_s)^{-0.5925960} \tag{21}$$

The enthalpy of saturated water, $H_{s.w.}$ can be calculated from the saturation pressure $P_s$ (psia) at inlet temperature $T_i$ by the following equations:

For saturation pressures, $P_s$, from 100 to 1000 psia;

$$H_{s.w.} = 90.7667 \, (P_s)^{0.2573} \tag{22}$$

For saturation pressures, $P_s$, from 1000 to 2000 psia;

$$H_{s.w.} = 64.576523 \, (P_s)^{0.30772701} \tag{23}$$

For saturation pressures, $P_s$, from 2000 to 2500 psia;

$$H_{s.w.} = 37.728252 \, (P_s)^{0.37894738} \tag{24}$$

For saturation pressures, $P_s$, from 2500 to 2900 psia;

$$H_{s.w.} = 0.13885164 \, (P_s) + 383.37582 \tag{25}$$

For saturation pressures, $P_s$, from 2900 to 3100 psia;

$$H_{s.w.} = 2.340899 \, (P_s)^{0.7293578} \tag{26}$$

The integral $\int C_p \, dT$ in Equation 1 is actually the difference between the enthalpy of superheated steam, $H_{s.h.s.}$ (BTU/lb) and of saturated steam, $H_{s.s.}$. The enthalpy of superheated steam $H_{shs}$, of course, is determined from the saturation pressure $P_s$ at the outlet temperature $T_o$ of the superheater-calorimeter 9, and may be given by the following equations:

$$H_{s.h.s.} = C_1 \, (T_o) - C_2 \tag{27}$$

For saturation pressures $P_s$ from 100 to 1500 psia and a temperature range of 60°R relative to the saturation temperature $T_s$, $C_1$ and $C_2$ in Equation 27 are:

$$C_1 = 3.8669 \, (10^{-4}) \, (P_s) + 0.68515998 \tag{28}$$

$$C_2 = 0.52188455 \, (P_s) - 800.58596 \tag{29}$$

For saturation pressures, $P_s$, from 1500 to 1800 psia and a temperature range of 60°R relative to the saturation temperature $T_s$, $C_1$ and $C_2$ in Equation 27 are:

$$C_1 = 3.6695311 \, (10^{-4}) \, (P_s) + 0.68515998 \tag{30}$$

$$C_2 = -0.54334247 \, (P_s) + 638.98077 \tag{31}$$

For saturation pressures, $P_s$, from 1800 to 1900 psia and a temperature range of 60°R relative to the saturation temperature $T_s$, $C_1$ and $C_2$ in Equation 27 are:

$$C_1 = 1.6224609 \, (10^{-3}) \, (P_s) - 1.5774 \tag{32}$$

$$C_2 = -1.9685750 \, (P_s) + 3252.1216 \tag{33}$$

For saturation pressures, $P_s$, from 1900 to 2100 psia and a temperature range of 80°R relative to the saturation temperature $T_s$, $C_1$ and $C_2$ in Equation 27 are:

$$C_1 = 0.18740234 \, (10^{-3}) \, (P_s) + 1.0388 \tag{34}$$

$$C_2 = -0.34689999 \, (P_s) + 293.93921 \tag{35}$$

For saturation pressures, $P_s$, from 2100 to 2200 psia and a temperature range of 50°R relative to the saturation temperature $T_s$, $$H_{s.h.s.} = C_1 \, (T_o) + C_2 \tag{36}$$

where:

$$C_1 = 2.4228515 \, (10^{-3}) \, (P_s) - 3.4304 \tag{37}$$

$$C_2 = -2.9101 \, (P_s) + 5467.8330 \tag{38}$$

For saturation pressures, $P_s$, from 2200 to 2300 psia and a temperature range of 50°R relative to the saturation temperature $T_s$, $C_1$ and $C_2$ in Equation 36 are:

$$C_1 = -6.464844 \, (10^{-5}) \, (P_s) + 2.0012 \tag{39}$$

$$C_2 = 9.3699999 \, (10^{-2}) \, (P_s) - 728.2688 \tag{40}$$

For saturation pressures, $P_s$, from 2300 to 2400 psia and a temperature range of 50°R relative to the saturation temperatures $T_s$, $$H_{s.h.s.} = C_1 \, (C_2)^{T_o} \tag{41}$$

where:

$$C_1 = 0.58749998 \, (10^{-2}) \, (P_s) + 178.99519 \tag{42}$$

$$C_2 = -0.000000154921 \, (P_s) + 1.0019379854202 \tag{43}$$

For saturation pressures, $P_s$, from 2400 to 2500 psia and a temperature range of 50°R relative to the saturation temperature $T_s$, $C_1$ and $C_2$ in Equation 41 are:

$$C_1 = -0.5666002 \, (P_s) + 1552.9216 \tag{44}$$

$$C_2 = 0.0000028979778 \, (P_s) + 0.9946109056473 \tag{45}$$

For saturation pressures, $P_s$, from 2500 to 2600 psia and a temperature range of 50°R relative to the saturation temperature $T_s$, $C_1$ and $C_2$ in Equation 41 are:

$$C_1 = 0.72375 \times 10^{-1} \, (P_s) - 44.492802 \tag{46}$$

$$C_2 = -0.0000005662441 \, (P_s) + 1.0032714605331 \tag{47}$$

For saturation pressures, $P_s$, from 2600 to 2700 psia and a temperature range of 40°R relative to the saturation temperature $T_s$, $C_1$ and $C_2$ in Equation 41 are:

$$C_1 = -0.75596249 \, (P_s) + 2109.1841 \tag{48}$$

$$C_2 = 0.0000062870981 \, (P_s) + 0.9854527711808 \tag{49}$$

For saturation pressures, $P_s$, from 2700 to 2800 psia and a temperature range of 40°R relative to the saturation temperature $T_s$, $C_1$ and $C_2$ in Equation 41 are:

$$C_1 = 0.13747708 (P_s) - 303.05280 \tag{50}$$

$$C_2 = -0.0000017535687(P_s) - 1.0071625709534 \tag{51}$$

For saturation pressures, $P_s$, from 2800 to 2900 psia and a temperature range of 40°R relative to the saturation temperature $T_s$, $C_1$ and $C_2$ in Equation 41 are:

$$C_1 = 0.13609375(P_s) - 299.08981 \quad (52)$$

$$C_2 = 0.0000013661385(P_s) + 1.0060777664185 \quad (53)$$

For saturation pressures, $P_s$, from 2900 to 3000 psia and a temperature range of 40°R relative to the saturation temperature $T_s$, $C_1$ and $C_2$ in Equation 41:

$$C_1 = -0.43377501(s) + 1353.5232 \quad (54)$$

$$C_2 = 0.0000049304567(P_s) + 0.9878002405767 \quad (55)$$

For saturation pressures, $P_s$, from 3000 to 3100 psia and a temperature range of 40°R relative to the saturation temperature $T_s$, $C_1$ and $C_2$ in Equation 41 are:

$$C_1 = 0.16759375(P_s) - 450.56 \quad (56)$$

$$C_2 = =0.0000025057783(P_s) + 1.0101269983566 \quad (57)$$

Equation 1 can now be rearranged to give the following equation:

$$Q = \dot{m}(1-x)(H_{s.s.} - H_{s.w.}) + \dot{m}(H_{s.h.s.} - H_{s.s.}) \quad (58)$$

The second term on the right side of Equation 58 represents the amount of heat for superheating the sample after the sample had been completely vaporized. The difference between the heat input to the superheater-calorimeter and the heat used to superheat is the amount of heat used to vaporize any moisture that was present in the sample:

$$Q_x = Q - m(H_{s.h.s.} - H_{s.s.}) \quad (59)$$

where $Q_x$ is the heat used to vaporize the moisture present in the sample in BTU/lb. The mass fraction of vapor contained in a sample, X, when entering the superheater-calorimeter can be determined from the following equation:

$$X = 1 - \frac{Q_x}{\dot{m}(H_{s.s.} - H_{s.w.})} \quad (60)$$

where X is the mass fraction of the sample that is vapor. The quality of steam is simply the fraction converted to a percentage.

The enthalpy of the sample entering the superheater-calorimeter can also be calculated. Knowing the quality of steam allows for the total enthalpy of the sample to be calculated as follows:

$$H_t = \dot{m}(1-x)(H_{s.w.}) + \dot{m}\,x\,(H_{s.s.} - H_{s.w.}) \quad (61)$$

where $H_t$ is the total enthalpy of the sample.

The saturation temperature, $T_s$ (°R), can be calculated from the saturation pressure, $P_s$ (psia), by the following equations developed.

For saturation pressures, $P_s$, from 100 to 1000 psia:

$$T_s = 118.77781\,(P_s)^{0.220036511} + 460 \quad (61.5)$$

For saturation pressures, $P_s$, from 1000 to 2000 psia:

$$T_s = 131.80284\,Ln\,(P_s) + 93.011665 \quad (62)$$

For saturation pressures, $P_s$, from 2000 to 2500 psia:

$$T_s = 146.69206\,Ln\,(P_s) - 19.504763 \quad (63)$$

For saturation pressures, $P_s$, from 2500 to 3200 psia:

$$T_s = 149.69206\,Ln\,(P_s) - 43.115791 \quad (64)$$

(2) Computer Simulation

Referring to FIG. 4B, an interactive computer program, written in the Fortran language, has been developed for a general purpose computer 16b to calculate the quality X of steam. The program simulates on-line operation and enables one to determine the saturation temperature $T_s$, latent heat of vaporization, $\lambda_s$, heat input $Q_x$ necessary for vaporizing the sample, enthalpy of the incoming steam sample $H_t$ (BTU/lb), and the quality of steam X. The only input data necessary are the inlet and outlet temperatures $T_i$ and $T_o$ and inlet pressure $P_1$ at superheater-calorimeter 9, the heat input Q to the same, and the mass flow rate $\dot{m}$ of sample stream. The equations identified in the blocks within computer 16b of FIG. 4B correspond to the functions defined by the same Equations 16 through 61, supra.

The computer program was made to default the value of the incoming temperature $T_i$ to the saturation temperature $T_s$. As stated above, this is correct for a quality of steam that is less than 100%, but not if the steam is superheated. In the actual practice of the present invention, it is recommended that the actual inlet temperature $T_i$ be used instead of the saturation temperature $T_s$, for the reason described above.

If the inlet and outlet temperatures $T_i$ and $T_o$ are $\pm 1\%$ of the actual, which the accuracy of most temperature sensors can fall easily within, the steam quality X is affected at most by $\pm 1.67\%$. At all the different conditions tested an error in the inlet pressure $P_i$ of $\pm 3\%$ produced a maximum error in the quality of steam of approximately $\pm 0.8\%$. This occurred at a high pressure (1600 psia) where the differences between the actual pressure and the pressure for the error introduced was 48 psia. This will affect the saturation temperature $T_s$, the enthalpy of saturated steam $H_{ss}$, saturated water $H_{sw}$, and superheated steam $H_{shs}$ on which their respective correlations depend. At higher pressures (i.e., 3000 psia), this $\pm 3\%$ error would inevitably produce an even greater error.

The total enthalpy $H_t$ of the sample entering the superheater-calorimeter 9 is also calculated in computer 16b. The enthalpy of the incoming sample is predicted with $\pm 1\%$ for pressure and temperature errors of $\pm 3\%$ and $+1\%$ respectively and 0% error for mass flow rate. It, however, increased to as much as $\pm 4\%$ for mass flow errors of $\pm 3\%$. This is due to the fact that both the enthalpy of saturated water and the latent heat of vaporization are multiplied by the mass flow rate, resulting in larger error in the enthalpy of the sample calculated.

(3) Results and Analysis

The first set of simulations were made only to test the correlations' range of applicability. Inlet pressures ranging from 200 to 3000 psia were chosen with various combinations of mass flow rate, heat input, and changes in both temperature and pressure within the calorimeter. The correlations and computer program were tested. Each of them worked well over these broad ranges of conditions tested.

The second set of runs tested more specific cases compared to the first set of simulation runs. The first run in this series assumed a large pressure and temperature change through the superheater-calorimeter. In the second run, a small pressure change and a large degree of superheating were assumed. The third run considered poor steam quality entering the superheater-calorimeter. The fourth and final run in these simulations assumed that the steam entering the superheater-calorimeter was in a superheated state. The results of these simulation runs are presented in Table 4. Steam quality and enthalpy calculations using the correlations developed for this invention were accurate for all the conditions tested.

The third set of runs tested a steam condition that was below 100% saturation. A different run studied the effect of a different variable. A ±3% error in the inlet or outlet pressures, a ±1% error in the inlet or outlet temperatures, and a ±3% in the mass flow rate measurement were assumed for runs in this series to see the effect of an assumed error in each of the variables on the accuracy of the calculated results. This test series is presented in Table 5. The temperature and pressure errors had a small effect on the calculated enthalpy of the incoming sample. However, a ±3% error in the mass flow rate measurement produced an error as much as ±3.26% in the enthalpy calculation. This is due to the fact that the mass flow rate is multiplied by the latent heat of vaporization and the enthalpy of saturated water, and a large error in this variable would inevitably lead to a large error in the enthalpy calculation. The steam quality did not change appreciably with any of the individual variable changes. For an outlet temperature error ±1%, the largest error produced in steam quality was ±0.745%.

actual operating conditions. Once again, a ±1% error in the inlet and outlet temperatures and a ±3% error in the inlet and outlet pressures were assumed. The mass flow rate measurement included an assumed ±5% error, 2% larger than the previously assumed ±3% error. The steam conditions tested were below and at the saturation level. The results of this final set of simulation runs are presented in Table 6. The greatest error (+3.28%) was produced in steam quality at the below saturation condition with a ±5% assumed error in the mass flow rate measurement. (See Run 9 in Table 6.) This is a consequence of the inaccurate value of the enthalpy of sample used in calculation of the quality.

TABLE 6

| Steam Conditions: | below Saturation | at Saturation |
|---|---|---|
| $P_i$ (psia) = | 1600 | 1000 |
| $P_o$ (psia) = | 1650 | 1050 |
| $T_i$ (°F.) = | 604.87 | 555.0 |
| $T_o$ (°F.) = | 644.87 | 590.0 |
| $\dot{m}$ (lb/hr) = | 10.0 | 100.0 |
| Quality (%) = | 91.76 | 100.01 |

| | | QUALITY | | QUALITY | |
|---|---|---|---|---|---|
| Run | ASSUMED ERROR | X (%) | Δ % | X (%) | Δ % |
| 1. | $\Delta T_i = \Delta T_o = +1\%$ | 93.28 | +1.63 | 100.84 | +0.84 |
| 2. | $\Delta T_i = \Delta T_o = -1\%$ | 90.24 | -1.66 | 99.19 | -0.81 |
| 3. | $\Delta P_i = \Delta P_o = +3\%$ | 90.99 | -0.84 | 99.67 | -0.33 |
| 4. | $\Delta P_i = \Delta P_o = -3\%$ | 92.50 | +0.806 | 100.34 | +0.34 |
| 5. | $\Delta P_i = \Delta P_o = +3\%$ $\Delta T_i = \Delta T_o = +1\%$ $\Delta \dot{m} = +3\%$ | 93.10 | +1.46 | 100.71 | +0.71 |

TABLE 4

| Conditions within Superheater-Calorimeter | | | | | Enthalpy | | | Quality | | |
|---|---|---|---|---|---|---|---|---|---|---|
| Through Superheater-Calorimeter | $P_i$ (psia) | $P_o$ (psia) | $T_i$ (°F.) | $T_o$ (°F.) | Hin (BTU/hr at 10 lbs/hr) | Hin* | Δ % | X (%) | X* (%) | Δ |
| 1. Large Temperature Large Pressure | 800 | 880 | 518.21 | 578.21 | 11,994 | 11,490 | −4.25 | 92.02 | 92.55 | — |
| 2. Small Pressure Large Superheat | 1400 | 1410 | 587.1 | 647.1 | 11,753 | 11,503 | −2.13 | 95.18 | 95.60 | — |
| 3. Poor Quality Into | 1600 | 1610 | 604.87 | 644.87 | 11,645 | 11,179 | −4.0 | 73.82 | 73.22 | — |
| 4. Superheated Into | 2600 | 2610 | 673.91 | 713.91 | 10,820 | — | — | 101.48 | 101.71 | + |

*Values from computer simulations
Δ %: Error percent in simulation results

TABLE 5

| Steam Conditions: | |
|---|---|
| $P_i$ (psia) = | 800 |
| $P_o$ (psia) = | 810 |
| $T_i$ (°F.) = | 518.21 |
| $T_o$ (°F.) = | 578.21 |
| $\dot{m}$ (lbs/hr) = | 10.0 |
| Quality (%) = | 92.55 |
| Enthalpy (BTU/lb) = | 1145.0 (Literature Value) |

| RUN | ASSUMED ERROR % | CALCULATED ENTHALPY Hin (BTU/lb) | Δ % | CALCULATED QUALITY X (%) | Δ % |
|---|---|---|---|---|---|
| 1. | $P_i = +3\%$ | 1146.0 | −0.10 | 92.09 | −0.497 |
| 2. | $P_i = -3\%$ | 1151.98 | +0.61 | 93.01 | +0.497 |
| 3. | $P_o = +3\%$ | 1149.1 | +0.35 | 92.55 | 0.0 |
| 4. | $P_o = -3\%$ | 1149.1 | +0.35 | 92.55 | 0.0 |
| 5. | $T_o = +1\%$ | 1153.3 | +0.72 | 93.15 | +0.648 |
| 6. | $T_o = -1\%$ | 1144.26 | −0.06 | 91.86 | −0.745 |
| 7. | $T_i = +1\%$ | 1149.1 | +0.35 | 92.55 | 0.0 |
| 8. | $T_i = -1\%$ | 1149.1 | +0.35 | 92.55 | 0.0 |
| 9. | $\dot{m} = +3\%$ | 1186.56 | +3.26 | 92.97 | +0.410 |
| 10. | $\dot{m} = -3\%$ | 1111.61 | −3.26 | 92.11 | −0.475 |

Δ %: Error percent in simulation results

In the fourth, and final simulation series, the effects of combinations of errors in all variables were studied. This test series is a more accurate representation of

| 6. | $\Delta P_i = \Delta P_o = -3\%$ $\Delta T_i = \Delta T_o = -1\%$ $\Delta \dot{m} = +3\%$ | 90.47 | −1.406 | 99.34 | +0.94 |
|---|---|---|---|---|---|
| 7. | $\Delta P_i = -3\%$ $\Delta T_i = -1\%$ $\Delta \dot{m} = -3\%$ $\Delta P_o = +3\%$ $\Delta T_o = +1\%$ | 93.42 | +1.81 | 100.94 | +0.94 |
| 8. | $\Delta P_i = -3\%$ $\Delta P_o = +3\%$ $\Delta T_i = -1\%$ $\Delta T_o = +3\%$ $\Delta \dot{m} = +3\%$ | 94.51 | +3.0 | 101.38 | +1.33 |
| 9. | $\Delta P_i = -3\%$ $\Delta P_o = +3\%$ $\Delta T_i = -1\%$ $\Delta T_o = +1\%$ $\Delta \dot{m} = +5\%$ | 94.77 | +3.28 | 101.45 | +1.45 |
| 10. | $\Delta P_i = -3\%$ $\Delta P_o = +3\%$ $\Delta T_i = -1\%$ $\Delta T_o = +1\%$ $\Delta \dot{m} = -5\%$ | 92.55 | +0.861 | 100.80 | +0.80 |

Δ %: Error percent in simulation results

From the foregoing it is apparent that the correlations relating the thermal properties of a vapor to temperature and pressure can be developed from the published data with accuracies suitable for their use in calculating the quality and the heat value of same in practicing the present invention. As shown above, the enthalpy of saturated steam $H_{ss}$ can be found from the saturation pressures $P_s$ ranging from 100 to 3100 psia with an accuracy of ±0.6% using Equations 16 through 21. The enthalpy of saturated water $H_{sw}$ can be found from the saturation pressures $P_s$ ranging from 100 to 3100 psia, with an accuracy of ±0.7% using Equations 22 through 26. The enthalpy of superheated steam $H_{shs}$ can be found from the saturation pressure $P_s$ and the superheated temperature $T_o$ at saturation pressures $P_s$ from 100 to 3100 psia, with an accuracy of ±1.0% using Equations 27 through 57. The correlations given as example were used in a computer model, and together provided an accurate estimation of steam quality within ±3%. The quality of steam X calculated is accurate within ±3% even with a ±1% error in the inlet and outlet temperature, a ±3% error in the inlet and outlet pressure, and a ±3% error in the mass flow rate $\dot{m}$. The enthalpy of a steam sample flowing into the superheater-calorimeter 9 was also calculated via the computer model with an accuracy of ±2.0%.

Other correlations were developed for this invention but were not included in the examples of simulation for the invention. For instance, the saturation pressure $P_s$ can be found from the saturation temperatures $T_s$ ranging from 790°R to 1160°R (100 psia to 3200 psia) with an accuracy of ±0.5%. The latent heat of vaporization $\lambda_s$ can be found from the saturation pressures $P_s$ ranging from 1000 to 3100 psia with an accuracy of ±1.0%. The enthalpy of saturated water $H_{sw}$ can be found from the saturation temperature $T_s$ for saturation temperatures ranging from 1044°R to 1160°R (1000 psia to 3100 psia) with an accuracy of ±0.65%.

The computer model and the simulation runs made show that the invention is most sensitive to mass flow rate measurements and not as sensitive to temperature and pressure measurements. Therefore, for accurate results of steam quality X and enthalpy measurement $H_t$, accurate mass flow measurements $\dot{m}$ are needed in the practice of the invention.

The sample stream, after having been superheated by superheater-calorimeter 9, will flow through the mass flowmeter 14, and the flow regulating valve 6 experiencing a small heat loss before returning to the vapor main 1. If this heat loss is controlled to approximate the heat input to superheater-calorimeter 9, the quality X and the heat value $H_t$ of the returning sample stream will approximate their initial values; so that the quality X and the heat value of the main vapor stream would not be affected appreciably by the practice of this invention. Since the above heat loss is prevented by thermal insulation 31, there is a small gain in the quality X and the heat value $H_t$ in the main vapor stream. The actual gain is determined by Equations 1-13, or by Equations 58-61, in which all the variables for the sample stream are replaced by the corresponding values for the main vapor. The temperature rise in the main vapor stream $T_o'-T_i'$ is proportional to the temperature rise for the sample stream $T_o-T_i$ as:

$$T_o'-T_i'=(T_o-T_i)\dot{m}/M \tag{65}$$

Where $T_i'$ and $T_o'$ are the initial and final temperatures of the main vapor stream, and M the mass flow rate of the main vapor. As shown in Equation 65, the temperature rise in the main vapor stream may be negligible since the ratio $\dot{m}/M$ is negligible in most cases. In cases where there is no temperature rise in the main vapor as a result of mixing with the sample stream, no superheating takes place in the main vapor stream, and therefore only the latent heat term $\lambda_s$ in heat balance Equation 1 or 58 need be considered. The increase in quality of the main vapor $\Delta X'$ may be readily determined by:

$$Q=M\Delta X'(H_{s.s.}-H_{s.w.}) \tag{66}$$

The resultant quality of main vapor X' will be the sum of the initial quality $X_o'$ and the increase in quality $\Delta X'$.

$$X'=X_o'+\Delta X' \tag{67}$$

Since the value of heat input Q in the superheater-calorimeter 9 is of an order of 100 watts and the ratio of $\dot{m}/M$ is very small (approximately proportional to the ratio of the cross sectional area of sampling inner tube 23 to that of vapor main 1), the heat input to the main vapor stream is so small that it can only contribute to the vaporization of some of the liquid in the main vapor and is not enough to superheat the main vapor to cause a temperature rise. For all practical purposes, Equation 66 is probably the only correction, if any, needed for a change in the quality of the main vapor.

Although water (steam) is most commonly used for generating power or heating in industry, it sometimes is not as effective when used to cool or heat extremely high temperatures as other liquids. These high temperatures occur frequently in the use of nuclear reactors, especially in the use of breeder reactors. In order to design a vapor-quality meter that will handle the vapor flow of liquid metals, a critical study of the metal's thermodynamic properties was made. The following sections of this disclosure gives important correlations of the thermodynamic properties of sodium, potassium, and cesium, that were developed for this invention.

As shown in Table 7, the specific heat (BTU/lb, °F.) of sodium was correlated over a temperature range of 373° K. to 1123° K. The breakup of the date into five temperature ranges was done in order to obtain the best correlations within a ±2% error. Table 8 lists the correlations for the saturation temperature of sodium as a function of the saturation pressure. The saturation temperature has units of degrees Kelvin and the saturation pressure, atmospheres. These equations cover a temperature range of 373° K. to 1073° K., a pressure range of $1.6\times10^{-10}$ atm to $4.4\times10^{-1}$ atm, and are accurate to within ±1%.

The correlations for the latent heat of vaporization $\lambda_s$, as a function of the saturation temperature $T_s$, of sodium are shown in Table 9. These equations hold for temperatures of 373° K. to 1073° K. Table 10 lists the equations relating the latent heat of vaporization $\lambda_s$, and the saturation pressure $P_s$, of sodium. These equations cover a pressure range of $1.3\times10^{-7}$ psia to 6.5 psia. In all cases the latent heat of vaporization is calculated in BTU/lb.

In the case of sodium metal, the enthalpy of the saturated liquid metal $H_{sl}$, was found as a function of both saturation temperature $T_s$, and saturation pressure $P_s$. Table 11 lists the equations for the enthalpy of the saturated liquid metal in BTU/lb as a function of the saturation temperature in °K. (degrees Kelvin). Table 12 correlated the enthalpy of the saturation liquid metal with the saturation pressure in atmospheres. Again, both relationships were found to be logarithmic, and accurate to within ±5%. The saturation temperature range holds for 373° K. to 1073° K., while the saturation pressure range holds for $1.6 \times 10^{-10}$ atm to $4.4 \times 10^{-1}$ atm.

TABLE 7

Correlation for the Specific Heat of Sodium as a Function of Temperature

| Temperature Ranges, °K. | Specific Heat, BTU/lb, °F. |
|---|---|
| 373–723 | $C_p = 0.2739722 + 21.48(1/T)$ |
| 723–923 | $C_p = 0.28660 + 11.75(1/T)$ |
| 923–998 | $C_p = 0.3134989 - 12.66(1/T)$ |
| 998–1048 | $C_p = 0.3290362 - 28.13(1/T)$ |
| 1048–1123 | $C_p = 0.3483940 - 48.49(1/T)$ |

TABLE 8

Correlations of Saturation Temperature and Pressure (atm) for Sodium

| Temperature Ranges, °K. | Saturation Temperature, °K. |
|---|---|
| 373–473 | $T_s = 788.26(P_s)^{0.0332}$ |
| 523–723 | $T_s = 980.95(P_s)^{0.0491}$ |
| 773–1073 | $T_s = 1130.35 \, (P_s)^{0.0739}$ |

TABLE 9

Equations for Latent Heat of Vaporation as a Function of Temperature for Sodium

| Temperature Ranges, °K. | Latent Heat, BTU/lb |
|---|---|
| 373–573 | $\log \lambda_s = (-0.000078)T_s + 3.319$ |
| 573–1073 | $\log \lambda_s = (-0.000122)T_s + 3.348$ |

TABLE 10

Equations for Latent Heat of Vaporization as a Function of Saturation Pressure (psia) for Sodium

| Pressure Ranges, psia | Latent Heat, BTU/lb |
|---|---|
| $1.251 \times 10^{-3} - 1 \times 10^{-3}$ | $\log \lambda_s = (-11.13)P_s + 3.284747$ |
| $1.000 \times 10^{-3} - 7.7 \times 10^{-2}$ | $\log \lambda_s = (-0.242)P_s + 3.2710$ |
| $7.654 \times 10^{-2} - 6.5118$ | $\log \lambda_s = (-0.005)P_s + 3.245742$ |

TABLE 11

Equations for the Enthalpy of Saturated Liquid Metal as a Function of Saturation Temperature for Sodium

| Temperature Ranges, °K. | Enthalpy, BTU/lb |
|---|---|
| 373–523 | $\log H_{sl} = -3.15986 + (1.99136) \log T_s$ |
| 523–873 | $\log H_{sl} = -1.63809 + (1.4321) \log T_s$ |
| 873–1073 | $\log H_{sl} = -1.08224 + (1.24128) \log T_s$ |

TABLE 12

Equations for the Enthalpy of Saturated Liquid Metal as a Function of Saturation Pressure (atm) for Sodium

| Pressure Ranges, atm | Enthalpy, BTU/lb |
|---|---|
| $1.58 \times 10^{-10} - 4.8 \times 10^{-4}$ | $\log H_{sl} = 2.648 + (0.0708) \log P_s$ |
| $4.84 \times 10^{-4} - 4.4 \times 10^{-1}$ | $\log H_{sl} = 2.704 + (0.0886) \log P_s$ |

Cesium and potassium were also studied. To date, however, data for both metals is not readily available. The only accessible information was that of the specific heat, $C_p$, as a function of the temperature, T. Table 13 shows the equations relating the specific heat of cesium in BTU/lb.°F. to temperature in °K. For the most part, the specific heat of cesium remains constant over the temperature range. There are slight changes in the specific heat from 273° K. to 400° K. From 400° K. to 1300° K. the specific heat of cesium is equal to 0.06 BTU/lb.°F.

The equations correlating the specific heat of potassium with temperature are shown in Table 14. The correlations cover a temperature range of 273° K. to 1423° K. The correlations were found to be accurate to within ±1%.

TABLE 13

Equations for the Specific Heat of Cesium

| Temperature Ranges, °K. | Specific Heat, BTU/lb, °F. |
|---|---|
| 273–373 | $C_p = 0.526(1/T) + 0.05403$ |
| 373–400 | $C_p = -0.23(1/T) + 0.1175$ |
| 400–1300 | $C_p = 0.06$ |

TABLE 14

Correlations for the specific Heat of Potassium

| Temperature Ranges, °K. | Specific Heat, BTU/lb, °F. |
|---|---|
| 273–323 | $C_p = -35.00(1/T) + 0.2997$ |
| 323–348 | $C_p = -15.00(1/T) + 0.2375$ |
| 348–373 | $C_p = 10.00(1/T) + 0.1650$ |
| 373–673 | $C_p = 8.2143(1/T) + 0.1698$ |
| 673–773 | $C_p = -5.00(1/T) + 0.1895$ |
| 773–973 | $C_p = -28.57(1/T) + 0.2197$ |
| 973–1173 | $C_p = -114.0(1/T) + 0.3060$ |
| 1173–1273 | $C_p = -200.0(1/T) + 0.380$ |
| 1273–1423 | $C_p = -243.0 \, (1/T) + 0.4137$ |

All the above correlations were tested for accuracy and applicability over each of the temperature and pressure ranges to see if they can be used in the invention for mass and energy balance. At this point, liquid sodium is as applicable as steam. Potassium and cesium, however, need more physical property data. The only accessible information found during an extensive literature survey was that of specific heat as a junction of temperature. Both metals are rare and expensive, and are therefore not considered to be economically viable. Two other alkaline metals studied are lithium and magnesium.

As may be apparent from the foregoing description, there are several points of particular note. First, the sample stream must be representative of the vapor flowing through the vapor main 1 at all times. Therefore design, construction, and location of the vapor sampling device are very important. Second, the accurate measurement of temperature, pressure, and mass flow rate is essential as it determines the accuracy of the vapor quality to be monitored. Especially, the vapor quality determination is most sensitive to mass flow rate measurements and is greatly affected by the temperature measurements; therefore, the accuracy and the reliability of the mass flowmeter and of the temperature sensing device are very important. Third, the complete vaporization of any liquids entrained in the vapor stream by the superheater-calorimeter 9 and the complete heat balance around the same are essential. For this reason, internal heater 19 is required instead of an external heater. Last, the accurate correlations of all the thermodynamic properties of the working fluid, both liquid and vapor states, are needed in order to perform a complete, accurate energy balance which is needed to determine the vapor quality. An assumption of a constant ratio of specific heat to latent heat, as made by others in the prior art, is totally inaccurate, and therefore unacceptable.

It will be understood that various changes in the details, steps and arrangement of parts, which have been herein described and illustrated in order to explain the nature of the invention may be made by those skilled in the art within the principle and scope of the invention as expressed in the appended claims. For example, the invention is applicable to monitoring the quality of any flowing condensable vapors for which all the necessary thermodynamic properties are known. It will also be understood other ways of making an energy balance using various thermodynamic properties of the working fluid are contemplated; the two methods shown in the foregoing discussion are merely illustrative and not limiting.

It may be obvious that the flow rate of the vapor, whose quality and enthalpy are being monitored according to the invention, can be directly monitored by relating the flow rate to the difference between the pressure $P_{si}$ at the sample intake point and the pressure $P_{so}$ at the sample returning point which are continuously measured. Therefore, the invention is capable of monitoring simultaneously the quality, enthalpy, and also the flow rate of a vapor.

I claim:

1. System for monitoring conditions for accurately determining the quality and enthalpy of a flowing vapor inside a pipe, said system comprising:
   a sampling device formed to be positioned inside the pipe for tapping off a small side stream of a representative sample of said vapor by utilizing the dynamic pressure of the flowing vapor;
   a superheater-calorimeter connected to said sampling device through a passage means for completely vaporizing any liquids entrained in the stream of sample vapor and then superheating the vaporized sample with a measurable input of heat;
   a flowmeter connected to said superheater-calorimeter through a passage means for accurately determining the mass flow rate of said vaporized sample;
   a sample returning device formed to be positioned inside the pipe at a point downstream of said sampling device and connected to said flowmeter through a passage means for returning the sample to the flowing vapor by utilizing the suction pressure of the flowing vapor;
   means for measuring the temperatures and pressures of the stream of sample vapor at the inlet and the outlet of said superheater-calorimeter;
   means for controlling and measuring the quantity of heat inputted to said superheater-calorimeter.

2. A system according to claim 1 wherein said sampling device and said returning device are placed together inside a case means with a screw-plug or the like for easier installation inside the pipe through the pipe wall.

3. A system according to claim 1 wherein said superheater-calorimeter includes an internal heater for heating the stream of sample vapor internally.

4. A system according to claim 3 wherein said internal heater is electrically energized.

5. A system according to claim 1 wherein said flowmeter is a mass flowmeter capable of directly metering the mass flow rate of the vaporized sample.

6. A system according to claim 5 wherein said mass flowmeter is of an electrothermal boundary-layer type flowmeter in which temperature sensing and heating elements are placed outside the pipe carrying said stream of sample vapor and do not obstruct the stream.

7. A system according to claim 1 wherein said means for measuring the temperatures are thin-band thermistors which are placed around the pipe carrying the stream of sample vapor and do not obstruct the stream.

8. A system according to claim 1 further comprising:
   computer means responsive to the measured temperatures, pressures, mass flow rate and quantity of heat input for determining the quality and enthalpy of the flowing vapor.

9. A system according to claim 1 wherein said superheater-calorimeter, said passage means connected to said sampling device and to said flowmeter are thermally insulated.

10. A system according to claim 1 wherein the pressure differential existing between the incoming stream of vapor sample at a point prior to entering said superheater-calorimeter and the returning stream of the sample at a point after leaving said flowmeter is monitored for determining the flow rate of said flowing vapor.

11. Apparatus for continuously monitoring conditions for accurately determining a thermodynamic property of a flowing vapor inside a pipe, comprising, in combination:
    sampling means formed to extend into the pipe for diverting therefrom a representative sample of the vapor;
    heating means operatively connected to said sampling means for heating the sample an amount sufficient to vaporize any liquids entrained therein and to superheat the vaporized sample;
    first means operatively connected to said heater means for producing an output signal indicative of the mass flowrate of the superheated sample;
    second sensing means operatively connected to said heating means for producing output signals indicative of the temperatures of the sample at the inlet and outlet of said heating means and of the pressure of the sample at the outlet of said heating means; and
    third sensing means operatively connected to said heating means for producing an output signal indicative of the quantity of the heat added to the sample by said heating means.

12. Apparatus according to claim 11 wherein said sampling means further comprises:
    a mounting head formed to be externally fixed to one side of the pipe; and
    an intake probe having an outer tube secured to said head and closed at one end for inserting diametrically to the other side of said pipe, an inner tube positioned within said outer tube and closed at one end for inserting midway into the pipe, a pair of annular seals positioned between said inner and outer tubes forming a chamber around the inserted length of said inner tube, a plurality of orifices distributed along the upstream side of said outer tube for equal annular mass flowrates at their centers, and an orifice in said inner tube positioned at the midpoint between said outer tube orifices.

13. Apparatus according to claim 12 further comprising:
    a return probe operatively connected to receive the sample from said flowmeter means for returning said sample to the pipe, said return probe having a return tube secured to said head and closed at one end for inserting into the pipe downstream of said intake probe, and an orifice in said return tube in the downstream side.

14. Apparatus according to claim 11 wherein said heater means further comprises:
    a shell connected between said sampling means and said flowmeter means for passing the vapor samples therethrough, and
    a heater spatially mounted within said shell for passing the sample thereabout.

15. Apparatus according to claim 14 wherein said heater means includes an adjustable source of electrical energy.

16. Apparatus according to claim 14 wherein said heater means further comprises:
a thermal insulator completely covering said shell and the inlet and outlet thereof.

17. Apparatus according to claim 11 wherein said mass flowmeter means is of the electrothermal boundary-layer type for permitting unobstructed flow.

18. Apparatus according to claim 11 wherein said second sensing means comprises:
thermistors formed into thin bands and placed around the inlet and outlet of said heater means.

19. Apparatus according to claim 11 further comprising:
valve means at the inlet to said heating means and at the outlet of said flowmetering means for regulating the pressure differential therebetween.

20. Apparatus for continuously monitoring conditions for accurately determining a thermodynamic property, such as quality or enthalpy, of a flowing vapor inside a pipe, comprising, in combination:

sampling means formed to extend into the pipe for diverting therefrom a representative sample of the vapor;

heating means operatively connected to said sampling means for heating the sample an amount sufficient to vaporize any liquids entrained therein and superheat the vaporized sample;

first means operatively connected to receive the sample from said heating means for producing an output signal indicative of the flowrate of the sample;

second sensing means operatively connected to said heating means for producing output signals indicative of the temperatures of the sample at the inlet and outlet of said heating means, and of the pressure at the outlet of said heating means;

third sensing means operatively connected to said heating means for producing an output signal indicative of the quantity of the heat added by said heating means; and combining means responsive to said output signals of said first, second and third means for producing a resultant signal indicative of the thermodynamic property of the vapor sample according to a heat balance around said heating means.

* * * * *

UNITED STATES PATENT AND TRADEMARK OFFICE
CERTIFICATE OF CORRECTION

PATENT NO. : 4,932,788

DATED : June 12, 1990

INVENTOR(S) : George C. Yeh

It is certified that error appears in the above-identified patent and that said Letters Patent is hereby corrected as shown below:

Column 7, line 15, "or" should read -- of --.

Column 8, lines 24-25, in equations (7) and (8) "$(P_1)$" should read -- $(P_i)$ --.

Column 14, equation (37), equation is unreadable and should read -- $C_1 = 2.4228515 \ (10^{-3}) \ (P_s) - 3.4714$ --.

Column 15, equation (59), "m" should read -- $\dot{m}$ --.

Column 15, equation (61.5), "0.220036511" should read -- 0.22036511 --.

Column 16, line 16, "$P_1$" should read -- $P_i$ --.

Column 17, Table 4, last column under "Quality", numbers are missing and should read, from the top, -- -0.57, -0.44, -0.81, +0.27 --.

Signed and Sealed this

Twenty-fourth Day of September, 1991

*Attest:*

HARRY F. MANBECK, JR.

*Attesting Officer*         *Commissioner of Patents and Trademarks*